(12) United States Patent
Pande et al.

(10) Patent No.: US 7,732,631 B2
(45) Date of Patent: Jun. 8, 2010

(54) ECO-FRIENDLY PROCESS FOR THE PREPARATION OF 2-CHLOROBENZYLIDENE-MALONONITRILE (CS)

(75) Inventors: Ambuja Pande, Madhya Pradesh (IN); Ramesh Chandra Malhotra, Madhya Pradesh (IN); Kumaran Ganesan, Madhya Pradesh (IN); Krishnamurthy Sekhar, Madhya Pradesh (IN); Vinita Dubey, Madhya Pradesh (IN)

(73) Assignee: Director General, Defence Research & Development Organisation, New Delhi (IN)

( * ) Notice: Subject to any disclaimer, the term of this patent is extended or adjusted under 35 U.S.C. 154(b) by 383 days.

(21) Appl. No.: 11/587,748

(22) PCT Filed: Apr. 7, 2005

(86) PCT No.: PCT/IN2005/000105

§ 371 (c)(1),
(2), (4) Date: Jan. 3, 2008

(87) PCT Pub. No.: WO2005/108350

PCT Pub. Date: Nov. 17, 2005

(65) Prior Publication Data

US 2008/0139837 A1 Jun. 12, 2008

(30) Foreign Application Priority Data

May 7, 2004 (IN) .......................... 840/DEL/2004

(51) Int. Cl.
*C07C 255/00* (2006.01)
(52) U.S. Cl. ...................................... 558/370
(58) Field of Classification Search ................. 558/370
See application file for complete search history.

(56) References Cited

U.S. PATENT DOCUMENTS 3,715,379 A * 2/1973 Berry et al. ................ 558/374
3,963,770 A 6/1976 Knapp

OTHER PUBLICATIONS

Shi, Da Quing et al., "The condensation of aromatic aldehydes with acidic methylene compounds in water"; Chinese Chemical Letters 2003, 14(12); pp. 1242-1243; ISSN 1001-8417.
Zhang, Shu et al., "Condensation of aromatic aldehydes with active methylene compounds in water"; Zuzhou Shifan Daxue Xuebao, Ziran Kexueban 2003; 21(2); pp. 42-45; ISSN 1007-6573.
Wang S., et al., The Knoevenagel condensation of aromatic aldehydes with malononitrile or ethyl cyanoacetate in the presence of CTMAB in water; Synthetic Communications 2001 31(5); pp. 673-677; ISSN 0039-7911.

* cited by examiner

*Primary Examiner*—Rei-tsang Shiao
(74) *Attorney, Agent, or Firm*—The Webb Law Firm

(57) ABSTRACT

An improved process for the preparation of 2-chlorobenzylidenemalononitrile (CS) comprising of the steps of: preparing malononitrile suspension by adding 5-20% (wt %) preferably 12-14% malononitrile to water while constantly stirring and then adding 0.05-0.5% (v/v) preferably 0.1-0% of a catalyst like piperidine, pyridine, 2-picoline, 3-picoline, 4-picoline or morpholine preferably piperidine piperidine with constant stirring at 20-30° C.; condensing the malononitrile suspension prepared in step (a) with 2-chlorobenzaldehyde by adding 10-15% (w/v) preferably 25-30%, of 2-chlorobenzaldehyde cover a period at 30-45 minutes so that the temperature of the reaction mixture remains below 50° C., constantly stirring for 20-40 minutes, then filtering the CS and drying it at 20-30° C. under water vacuum for 3-5 hrs.

7 Claims, No Drawings

ECO-FRIENDLY PROCESS FOR THE PREPARATION OF 2-CHLOROBENZYLIDENE-MALONONITRILE (CS)

FIELD OF INVENTION

This invention relates to an improved and eco-friendly process for the preparation of 2-Chlorobenzylidenemalononitrile [CS, (2-chlorophenyl)methylene propanedinitrile] using water as a solvent.

PRIOR ART

2-Chlorobenzylidenemalononitrile (CS) was first reported by Corson and Stoughton and was introduced as riot control agent in 1958. It is a white crystalline solid, ten times more potent than ω-chloroacetophenone, a well known riot control agent. To produce immediate effects on the eyes and respiratory tract, 4 mg/m$^3$ CS is sufficient. Exposure to CS results in immediate burning sensation in eyes, accompanied by copious flow of tears and involuntary closing of eyes, irritation of respiratory tract results in sneezing, tightness in chest with difficulty in breathing and coughing. In high concentrations, CS causes nausea and vomiting.

One of the process known in the art, for the synthesis of CS, involves Knoevenagel condensation of 2-chlorobenzaldehyde and malononitrile, either using organic solvents and pyridine or in absence of organic solvents by grinding. The method reported by Corson and Stoughton involves Knoevenagel condensation of 2-chlorobenzaldehyde with malononitrile in the presence of pyridine using cyclohexane as solvent for the reaction. Another method (U.S. Pat. No. 3,963,770) uses methanol as solvent for the synthesis of CS.

The main disadvantage of these methods is that large quantity of cyclohexane or methanol is required.

Another disadvantage of these methods is that the organic solvents, cyclohexane and methanol are toxic and inflammable.

Yet another disadvantage of these methods is that isolation of CS is difficult at room temperature due to its solubility in both the solvents.

Still another disadvantage of these methods is that due to the toxic and inflammable nature of the effluent, the disposal of effluent is difficult and hence these processes are not environmental and eco-friendly.

Yet another disadvantage of these methods is that the cyclohexane is not recycled in the former process, therefore the process is not, cost effective.

Another known process in the art for synthesis of CS involves solvent free Knoevenagel condensation of 2-chlorobenzaldehyde and malononitrile by grinding.

The major drawback of this method is that the reaction is applicable to laboratory scale but not suitable for upscaling the process.

Another drawback of this method is that isolation and purification of the product is difficult since no solvent is used in the synthesis.

Still another drawback of this method is that purity of the CS obtained is mainly dependent on the efficiency of the grinding.

Yet another drawback of this method is that it is a heterogeneous reaction and difficult to find the completion of the reaction if the grinding efficiency is poor.

Other drawback of this method is that it requires special equipment, thus this process is not cost-effective also.

There is a need to develop an improved eco-friendly and cost effective method for the preparation of 2-chlorobenzylidenemalononitrile (CS) that can easily be up scaled to manufacturing process.

OBJECTS OF THE PRESENT INVENTION

The main object of the present invention is to provide an improved process for the presentation of 2-chlorobenzylidenemalononitrile (CS).

Another object of the present invention is to provide an improved process for the preparation of CS, which gives CS of high purity.

Yet another object of the present invention is to provide an improved process for the preparation of CS wherein the water used as solved is recycled to reduce the effluent load.

Still another object of the present invention is to provide an improved process for the preparation of CS where in water is used as solvent.

Further object of the present invention is to provide an improved process for the preparation of CS wherein the effluent can be disposed off easily without any environmental pollution.

Yet further object of the present invention is to provide an improved process for the preparation of CS which is cost effective.

Still further object of the present invention is to provide an improvement method for the preparation of CS which does not require any special equipment.

The yield and purity of CS obtained is >99.5% and the melting point is 92-94° (Reported mp 94° C.). The process is simple, does not pollute the environment and is eco-friendly.

DESCRIPTION OF INVENTION

According to this invention there is provided an improved process for the preparation of 2-chlorobenzylidenemalononitrile (CS) comprising of the steps of:

(a) preparing malononitrile suspension by adding 5-20% (wt %) preferably 12-14% malononitrile to water while constantly stirring and then adding 0.05-0.5% (v/v) preferably 0.1-03% of a catalyst like piperidine, pyridine, 2-picoline, 3-picoline, 4-picoline or morpholine preferably piperidine with constant stirring at 20-30° C.;

(b) condensing the malononitrile suspension prepared in step (a) with 2-chlorobenzaldehyde by adding 10-15% (v/v) preferably 25-30%, of 2-chlorobenzaldehyde cover a period at 30-45 minutes so that the temperature of the reaction mixture remains below 50° C., constantly stirring for 20-40 minutes, then filtering the CS and drying it at 20-30° C. under water vacuum for 3-5 hrs.

The process of the present invention for the preparation of 2-chlorobenzylidene malononitrile (CS) comprises of following steps:

Step (i): Preparation of Malononitrile Suspension:

In a bottom flask equipment with water condenser, mechanical stirrer and pressure-equalizing funnel, 5-20% (wt %) of malononitrile preferably 12-14% (wt %) is added in water with stirring. To this, 0.05-05% v/v preferably 0.1-0.3% v/v of catalyst like piperidine, pyridine, 2-picoline, 3-picoline, 4-picoline or morpholine preferably piperidine is added with continuous stirring at 20-30° C.

Step (ii) Condensation with 2-chloroberzaldehyde

To the malononitrile suspension prepared in step (i), 10-15% (w/v) of 2-chlorobenzaldehyde preferably 25-30% (w/v) is added over a period of 30-46 minutes so that the temperature of the reaction does not go beyond 50° C., and the reaction mixture is stirred continuously for another 20-40 minutes. The white crystalline solid CS is filtering and dried at 20-30° C. under water vacuum for 3-5 hrs. The filtrate (mother liquor) is used for the preparation of CS in subsequent batches.

The generation of effluent is reduced by using the mother liquor repeatedly for 5-50 batches, preferably 10-15 batches, Instead of using fresh water for each batch, for safe disposal of the mother liquor obtained after 5-50 cycles, it is taken in a three-necked round bottom flask equipment with water condenser abd mechanical stirrer. To this flask sodium hydroxide (equivalent to 1 to 25% w/v, preferably 5-10% w/v of effluent) is added slowly and the mixture is refluxed for 2-6 hrs. After cooling the mixture to 20-30° C., the effluent is safely disposed off in the municipal drainage system.

In every batch, the yield and purity of CS obtained is >99.5% and the melting point is 92.94° C. (Reported mp 94° C.).

This invention will now be illustrated with a working example, which is intended to be typical example to explain the technique of the present invention and is not intended to be taken restrictively to imply any limitation to the scope of the present invention.

WORKING EXAMPLES

Example 1

Water (5000 ml) was taken in a three-necked round bottom flask equipped with thermometer, pressure equalizing funnel and magnetic stirrer. To this malononitrile (660.6 g, 10 moles) was added and then piperidine (10 ml, 0.1 mole) was added with constant stirring. To this 2-chlorobenzaldehyde (2108 g, 15 moles) was added slowly with continuous stirring through pressure equalizing funnel. The temperature of the reaction mixture was maintained at 50° C. during addition of 2-chlorobenzaldehyde. The white crystalline solid CS thus obtained was filtered and then dried under vacuum (25 mm).

Mother liquor obtained after filtration of white solid was recycled for the preparation of CS by the same procedure as mentioned above for ten times. The mother liquor obtained after 10 cycles was taken in three-necked round bottom flask, to this sodium hydroxide 250 g was added and the mixture was refluxed for 4 hrs. After cooling the mixture to 25° C. and after analysis, the effluent was disposed off in the municipal drainage system. The yield and purity of CS was >99.5% and the melting point is 92-94° C. (Reported mp 94° C.).

Example II

Water (5000 ml) was taken in a three neck round bottom flask equipped with thermometer, pressure equalizing funnel and magnetic stirrer. To this malononitrile (660.6 g, 10 moles) was added and then piperidine (10 ml, 0.1 mole) was added with constant stirring. To this 2-chloroberzaldehyde (1405 g, 10 moles) was added slowly with continuous stirring through pressure equalising funnel. The temperature of the reaction mixture was maintained at 50° C. during addition of 2-chloroberzaldehyde. The while crystalline solid CS thus obtained was filtered and then dried under vacuum (25 mm).

Mother liquor obtained after filtration of white solid was recycled for the preparation of CS by the same procedure as mentioned above. The mother liquor obtained after 10 cycles was taken in three-necked round bottom flask, to this sodium hydroxide 250 g was added and the mixture was refluxed for 4 hrs. After cooling the mixture to 25° C. and after analysis, the effluent was disposed off in the municipal drainage system. The yield and purity of CS was >99.5% and the melting point was 92-94° C. (Reported mp 94° C.).

Example III

Water (5000 ml) was taken in a three-necked round bottom flask equipped with thermometer, pressure equalizing funnel and magnetic stirrer. To this malonontrile (991 g, 15-moles) was added and then piperidine (10 ml, 0.1 mole) was added with constant stirring. To this 2-chlorobenzaldehyde (1405 g, 10 moles) was added slowly with continuous stirring through pressure equalizing funnel. The temperature of the reaction mixture was maintained at 50° during addition of 2-chlorobenzaldehyde. The white crystalline solid CS thus obtained was filtered and then dried under vacuum (25 mm).

Mother liquor obtained after filtration of white solid was recycled for the preparation of CS by the same procedure as mentioned above. The mother liquor obtained after 10 cycles was taken in three-necked round bottom flask, to this sodium hydroxide 250 g was added and the mixture was refluxed for 4 hrs. After cooling the mixture to 25° C. and after analysis, the effluent was disposed off in the municipal drainage system. The yield and purity of CS was >99.5% and the melting point was 92-94° C. (Reported mp 94° C.).

It is to be understood that the process of the present invention is susceptible to modification, changes, adaptations by those skilled in the art, such modifications, changes, adaptation are intended to be within the scope of the present invention which is further set forth under the following claims:

The invention claimed is:

1. An eco-friendly improved process for the preparation of 2-chlorobenzylidenemalononitrile (CS), comprising the steps of:
   (a) preparing malononitrile suspension by adding 5-20% (wt %) malononitrile to water while constantly stirring and then adding 0.05-0.5% (v/v) of a catalyst selected from the group consisting of piperidine, pyridine, 2-picoline, 3-picoline, 4-picoline and morpholine with constant stirring at 20-30° C.;
   (b) condensing the malononitrile suspension prepared in step (a) with 2-chlorobenzaldehyde by adding 10-15% (w/v) of 2-chlorobenzaldehyde, cover for a period at 30-45 minutes so that the temperature of the reaction mixture remains below 50° C., constantly stirring for 20-40 minutes, then filtering the CS and drying it at 20-30° C. under water vacuum for 3-5 hours.

2. The improved process for the preparation of CS as claimed in claim 1, wherein the generation of effluent is reduced by recycling the filtrate (mother liquor) obtained in step (b) for 5-50 batches of preparation of CS.

3. The improved process for the preparation of CS as claimed in claim 2, wherein 10-15 batches of CS are prepared.

4. The improved process for the preparation of CS as claimed in claim 2, wherein the mother liquor obtained after recycling for 5-50 batches is treated with sodium hydroxide equivalent to 1-25% (w/v), refluxing for 2-6 hours, then cooling to 20-30° C. before disposing.

5. The improved process for the preparation of CS as claimed in claim 4, wherein treatment of the mother liquor with sodium hydroxide is equivalent to 5-10% (w/v) of effluent.

6. The improved process for the preparation of CS as claimed in claim 1, wherein the process is performed in water.

7. An eco-friendly improved process for the preparation of 2-chlorobenzylidenemalononitrile (CS), comprising the steps of:

(a) preparing malononitrile suspension by adding 12-14% (wt %) malononitrile to water while constantly stirring and then adding 0.1-0.3% (v/v) of a catalyst, wherein the catalyst is piperidine with constant stirring at 20-30° C.;

(b) condensing the malononitrile suspension prepared in step (a) with 2- chlorobenzaldehyde by adding 25-30% (w/v) of 2-chlorobenzaldehyde, cover for a period at 30-45 minutes so that the temperature of the reaction mixture remains below 50° C., constantly stirring for 20-40 minutes, then filtering the CS and drying it at 20-30° C. under water vacuum for 3-5 hours.

* * * * *